United States Patent [19]

Miranda et al.

[11] Patent Number: 5,091,186

[45] Date of Patent: Feb. 25, 1992

[54] BIPHASIC TRANSDERMAL DRUG DELIVERY DEVICE

[75] Inventors: Jesus Miranda, Miami, Fla.; Gary W. Cleary, San Mateo, Calif.

[73] Assignee: Cygnus Therapeutic Systems, Redwood City, Calif.

[21] Appl. No.: 394,096

[22] Filed: Aug. 15, 1989

[51] Int. Cl.$^5$ .......................................... A61F 13/02
[52] U.S. Cl. .................................. 424/448; 424/419; 424/447
[58] Field of Search ................ 424/473, 448, 449, 426

[56] References Cited

U.S. PATENT DOCUMENTS

| | | | |
|---|---|---|---|
| 3,742,951 | 7/1973 | Zaffaroni | 424/434 |
| 3,797,494 | 3/1974 | Zaffaroni | 424/434 |
| 3,854,480 | 12/1974 | Zaffaroni | 424/424 |
| 3,921,636 | 11/1975 | Zaffaroni | 424/432 |
| 3,923,939 | 12/1975 | Baker et al. | 264/49 |
| 3,964,482 | 6/1976 | Gerstel et al. | 604/890.1 |
| 3,996,934 | 12/1976 | Zaffaroni | 604/890.1 |
| 4,036,227 | 7/1977 | Zaffaroni et al. | 424/427 X |
| 4,336,243 | 6/1982 | Sanvordeker et al. | 424/486 X |
| 4,533,540 | 8/1985 | Blank | 424/486 |
| 4,559,222 | 12/1985 | Enscore et al. | 424/486 |
| 4,601,893 | 7/1986 | Cardinal | 424/473 X |
| 4,605,548 | 8/1986 | Ushiyama et al. | 424/449 |
| 4,615,699 | 10/1986 | Gale et al. | 424/448 |
| 4,650,484 | 3/1987 | Shaw et al. | 424/448 |
| 4,654,209 | 3/1987 | Leslie et al. | 424/80 |
| 4,655,766 | 4/1987 | Theeuwes et al. | 604/891.1 |
| 4,661,105 | 4/1987 | Gale | 424/448 |
| 4,666,441 | 5/1987 | Andriola et al. | 424/448 |
| 4,681,584 | 7/1987 | Gale et al. | 424/449 |
| 4,698,062 | 10/1987 | Gale et al. | 424/449 |
| 4,704,119 | 11/1987 | Shaw et al. | 424/448 |
| 4,717,568 | 1/1988 | Eckenhoff et al. | 424/469 |
| 4,723,957 | 2/1988 | Magruder et al. | 424/78 |
| 4,751,087 | 6/1988 | Wick | 424/449 |
| 4,776,850 | 10/1988 | Guse et al. | 604/304 |
| 4,778,678 | 10/1988 | Guse et al. | 424/487 |
| 4,784,857 | 11/1988 | Berry et al. | 424/449 |
| 4,786,282 | 11/1988 | Wagle et al. | 604/307 |
| 4,830,690 | 7/1989 | Ranade | 424/486 |
| 4,834,982 | 5/1989 | Putter | 424/470 X |
| 4,898,920 | 2/1990 | Lee et al. | 424/488 X |
| 4,906,643 | 3/1990 | Cleary et al. | 424/78 |
| 4,954,340 | 9/1990 | Hosaka et al. | 424/449 X |

FOREIGN PATENT DOCUMENTS

| | | |
|---|---|---|
| 0033615 | 1/1981 | European Pat. Off. . |
| 0227252 | 7/1987 | European Pat. Off. . |
| 0249343 | 12/1987 | European Pat. Off. . |
| 0279986 | 8/1988 | European Pat. Off. . |
| 2100605 | 1/1983 | United Kingdom . |

OTHER PUBLICATIONS

H. Cornell, *Medical World News* (10 Oct. 1988), pp. 13-14.

*Primary Examiner*—Thurman K. Page
*Assistant Examiner*—Leon R. Horne
*Attorney, Agent, or Firm*—Morrison & Foerster

[57] ABSTRACT

A transdermal drug delivery system in which drug delivery is biphasic is provided. Drug is delivered at a therapeutically effective rate during an initial, delivery phase, typically of about 10 to 14 hours, followed by a subsequent, secondary phase during which virtually no drug is delivered. Substantially all of the drug initially loaded into the device is delivered within the initial, delivery phase.

19 Claims, 4 Drawing Sheets

BIPHASIC TRANSDERMAL DRUG DELIVERY DEVICE

TECHNICAL FIELD

The present invention relates generally to the field of transdermal drug delivery, and more particularly relates to a novel transdermal system in which drug delivery is biphasic. That is, drug is delivered at a therapeutically effective rate during an initial delivery phase, followed by a secondary phase in which substantially no drug is delivered.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences -- e.g., gastrointestinal irritation and the like -- are eliminated as well. Transdermal drug delivery also makes possible a high degree of control over blood concentrations of any particular drug.

The vast majority of transdermal systems are designed so as to deliver a drug substantially continuously throughout the wearing period. For many drugs, however, continuous delivery poses the potential problem of drug tolerance. For such drugs, a continuous delivery patch must removed periodically during the wearing period so as to prevent development of tolerance. The inconvenience of periodic patch removal can in turn create problems with patient compliance and thus with drug efficacy as well.

One drug which is currently administered transdermally is nitroglycerin, a vasodilator useful in the treatment of angina pectoris and congestive heart failure. Several transdermal systems currently on the market provide continuous plasma levels of nitroglycerin over a 24-hour period (e.g., the "Transderm Nitro" ® system of ALZA Corporation, Palo Alto, California). However, there is increasing evidence that continuous delivery of nitroglycerin causes development of tolerance in the patient, with resulting loss of efficacy. Recently, this factor has caused certain regulatory authorities to advise against the use of delivery systems that will administer nitroglycerin continuously without a washout period at some time during the day An additional problem which is common to most transdermal drug delivery systems is residual drug, i.e., drug which remains in the device after use. Highly expensive drugs are costly to discard, and dangerous or controlled narcotic drugs can be diverted for abuse or present other uncontrollable hazards The present invention is addressed to these deficiencies in the art, and provides a system wherein (1) drug delivery is not continuous but biphasic, and (2) substantially no drug remains in the device after use.

DESCRIPTION OF THE PRIOR ART

The following references are directed to transdermal drug delivery devices stated to be useful in the administration of vasodilators and other cardiovascular drugs U.S. Pat. Nos. 3,742,951 to Zaffaroni, 3,797,494 to Zaffaroni, 3,854,480 to Zaffaroni, 3,921,636 to Zaffaroni, 3,923,989 to Baker et al., 3,964,482 to Gerstel et al., 3,996,934 to Zaffaroni, 4,650,484 to Shaw et al , 4,661,105 to Gale, 4,704,119 to Shaw et al., 4,717,568 to Eckenhoff et al., and 4,723,957 to Magruder et al.

References which relate to the transdermal administration of nitroglycerin, specifically, include U.S. Pat. Nos. 4,533,540 to Blank, 4,559,222 to Enscore et al , 4,615,699 to Gale et al., 4,654,209 to Leslie et al , 4,655,766 to Theeuwes et al., 4,661,441 to Andriola et al., 4,681,454 to Gale et al., 4,681,584 to Gale et al., 4,751,087 to Wick, 4,776,850 to Guse et al., 4,778,678 to Guse et al., 4,784,857 to Berry et al., and 4,786,282 to Wagle et al.

U.S. Pat. No. 4,698,062 to Gale et al. describes a biphasic transdermal system in which drug such as nitroglycerin is administered at a relatively high flux during a first delivery period and at a lower flux during a second delivery period. In contrast to the teaching of this patent, applicants' invention involves delivery of substantially all of the drug contained within the device, i.e., during an initial delivery period, and substantially no drug delivery during the subsequent, secondary phase. H. Cornell, *Medical World News* (Oct. 10, 1988), also discloses a biphasic system for the transdermal delivery of nitroglycerin which appears to be similar to the system of the '062 patent.

SUMMARY OF THE INVENTION

It is a primary object of the invention to provide a biphasic transdermal drug delivery device which overcomes the above-stated deficiencies of the prior art.

It is also an object of the invention to provide a biphasic transdermal drug delivery device for delivering a drug at a therapeutically effective rate during an initial delivery phase, but which delivers substantially no drug during a subsequent secondary phase.

It is another object of the invention to provide such a biphasic transdermal drug delivery device in which substantially all of the drug contained therein is delivered during the initial, delivery phase.

It is a further object of the invention to provide such a biphasic transdermal drug delivery device in which the latter objects are achieved by selection of appropriate diffusion and solubility parameters.

It is still a further object of the invention to provide such a biphasic transdermal drug delivery device for the administration of nitroglycerin.

Additional objects, advantages and novel features of the invention will be set forth in part in the description which follows, and in part will become apparent to those skilled in the art upon examination of the following, or may be learned by practice of the invention.

In its primary aspect, the invention comprises a biphasic transdermal drug delivery device for delivering a drug at therapeutically effective rates during an initial, delivery phase of about 10 to 14 hours, but which during a subsequent, secondary phase, delivers substantially no drug, the device comprising:

(a) a backing layer that is substantially impermeable to the drug and defines the face surface of the device; and (b) an adhesive drug reservoir layer that defines the basal surface of the device during use and contains the drug, wherein the diffusion coefficient of the drug in the reservoir layer is at least about $10^{-8}$ cm$^2$/sec, and the solubility of the drug in the reservoir layer is less than about 10 wt %.

In another aspect, the invention is specifically directed to a biphasic system for the transdermal administration of nitroglycerin.

DETAILED DESCRIPTION OF THE INVENTION

Figure 1:
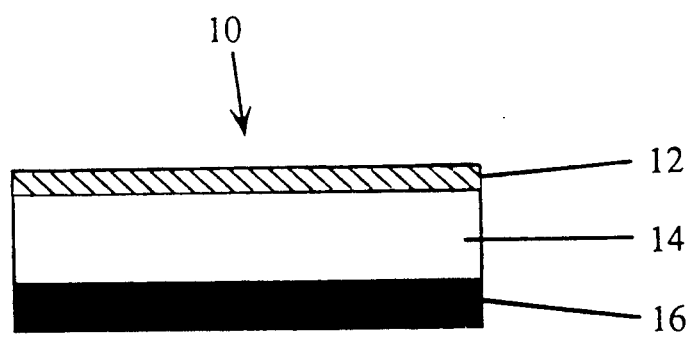
FIG. 1 is a schematic, cross-sectional representation of a transdermal delivery device of the invention.

Referring now to FIG. 1, the transdermal drug delivery device of the invention is shown generally at 10. The device is in the form of a laminated composite that is adapted to be adhered to a predetermined area of unbroken skin or mucosal tissue. The device is designed to provide biphasic and complete drug delivery, i.e., substantially complete delivery of drug during an initial delivery period, followed by a secondary phase wherein virtually no drug is delivered. The individual layers of the device include a backing layer 12 that is substantially impermeable to the drug and defines the upper, face surface of the device, and an adhesive drug reservoir layer 14 that defines the basal surface of the device during use and contains the selected drug or drugs. Other materials to be co-administered with the selected drug are contained in drug reservoir 14 as well, e.g., enhancers, solubilizers, or the like.

The backing layer 12 functions as the primary structural element of the device and provides the device with much of its flexibility and drape. The backing layer also serves as a protective covering to prevent loss of drug (an/or vehicle, solubilizer or permeation enhancer, if present) via transmission through the upper surface of the device. Backing layer 12 may also be used to impart the device with a desirable or necessary degree of occlusivity which in turn causes the area of skin on which the device is placed to become hydrated. In such a case, a layer is selected that has a level of water vapor transmissibility that makes the device occlusive to the degree required to cause the area of skin to be hydrated. It is then preferable that the device provide at least about 90% hydration, more preferably at least about 95% hydration of the skin, as measured by a dielectric hydration probe available from Dr. Howard Maibach, U.C.S.F., San Francisco, California. Such occlusivity is desirable when drugs such as estradiol or other steroids are being administered. Of the drug being administered is such that skin hydration is not necessary or desirable, it is preferable to use layers that provide a composite that is "breathable", i.e., transmits water vapor from the skin to the atmosphere. Such breath ability contributes to the nonocclusive nature of the composite and lessens the likelihood that the area of skin on which the composite is worn will become highly hydrated and irritated.

Backing 12 is preferably made of a sheet or film of a preferably flexible material that is substantially impermeable to the selected drug. The layer is preferably on the order of 0.0005" to 0.003" in thickness, and may or may not contain pigment. The layer is preferably of a material that permits the device to mimic the contours of the skin and be worn comfortably on areas of skin, such as at joints or other points of flexure, that are normally subjected to mechanical strain with little or no likelihood of the device disengaging from the skin due to differences in the flexibility or resiliency of the skin and the device. Examples of elastomeric polymers that are useful for making backing layer 12 are polyether block amide copolymers (e.g., PEBAX copolyers), polyethylene methyl methacrylate block copolymers (EMA) such as NUKRELL polyers, polyurethanes such as PELLATHANE or ESTANE polymers, silicone elatomes, polyester block copolymers that are composed of hard and soft segments (e.g., HYTREL polymers), rubber-based polyisobutylene, styrene, and styrene-butadiene and styrene-isoprene copolymers. Polymers that are flexible include polyethylene, polypropylene, and polyesters, e.g., polyester terephthalate (PET), which may be in the form of films or laminates. The backing layer may also be comprised of a laminate of two or more of the aforementioned polymers, e.g., a polyethylene/polyester laminate. The preferred polymer or polymers used for the backing will depend on the material or drug incorporated into the device and on the nature of any vehicles, solubilizers, or the like that are used.

Drug reservoir layer 14, which plays the principal role in determining the rate at which drug is released from the device, is a pressure-sensitive skin contact adhesive comprised of a pharmaceutically acceptable material. By "pharmaceutically acceptable" is meant a material which does not interfere with the biological effectiveness of the drug administered and which is not for any reason biologically or otherwise undesirable.

Examples of suitable materials for drug reservoir layer 14 include polyethylenes, polysiloxanes, polyisobutylenes, polyacrylates, polyurethanes, plasticized ethylene-vinyl acetate copolymers, low molecular weight polyether block amide copolymers (PEBAX copolymers), tacky rubbers such as polyisobutene, polystyrene-isoprene copolymers, polystyrene-butadiene copolymers, and mixtures thereof. The particular polymer(s) used for the drug reservoir layer will depend on the drug, vehicle, enhancer, etc., selected.

Prior to use, device 10 includes a release liner 16. Just prior to use, this layer is removed from the device to expose adhesive drug reservoir layer 14. The release liner will normally be made from a drug/vehicle/enhancer impermeable material that is inherently "strippable" or rendered so by techniques such as silicone or fluorocarbon treatment.

Device 10 need not include a means for controlling the rate at which either the drug or the enhancer is administered to skin. Instead, the release kinetics of the drug from the bandage can be controlled by the material selected for the drug reservoir layer and by the degree of drug loading. Typically, over the effective lifetime of the device, drug is presented to the skin at a rate in excess of the rate that the treated area of skin is able to absorb. It will be appreciated, however, that depending upon the particular drug (and enhancer when one is needed) that is being administered, that it may be necessary or desirable to include an element in the device that will control the release rate of the drug and/or the enhancer. Such elements are known in the art.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the inventive device are anti-inflammatory drugs, analgesics, antiarthritic drugs, tranquilizers, narcotic antagonistis, antiparkinsonism agents, anticancer drugs, immunosuppression agents, antiviral agents, antibiotic agents, appetite suppressants, antiemetics, anticholinergics, antihistaminics, antimigraine agents, coronary, cerebral or peripheral vasodilators, anti-anginals, e.g., calcium channel blockers, hormonal agents, contraceptive agents, antithrombotic agents, diuretics, antihypertensive agents, cardiovascular drugs, chemical dependency drugs, and the like. The appropriate drugs of such types are capable of permeating through the skin either inherently or by virtue of treatment of the skin with a percutaneous absorption enhancer. Because the size of the device is limited for patient acceptance reasons, the preferred drugs are those which are effective at low concentration in the blood stream. Examples of specific drugs are steroids such as estradiol, progesterone, norethindrone, norethindrone acetate, levonorgestrel, ethynodiol diacetate, norgestamate, gestadene, desogestrel, 3-keto desogestrel, demegestone, promegestrone, testosterone, hydrocortisone, and their esters; nitro compounds such as amyl nitrate, nitroglycerin and isosorbide nitrates; amine compounds such as nicotine, chlorpheniramine, terfenadine and triprolidine; oxicam derivatives such as piroxicam; mucopolysaccharidases such as thiomucase; opioids such as buprenorphine, fentanyl and fentanyl derivatives or analogs, naloxone, codeine, dihydroergotamine, pizotiline, salbutamol and terbutaline; prostaglandins such as those in the PGA, PGB, PGE and PGF series, e.g., misoprostol and enprostil, omeprazole, imipramine: benzamides such as metoclopramine and scopolamine; peptides such as growth releasing factor, growth factors (EGF, TGF, PDGF and the like), and somatostatin; clonidine; dihydropyridines such as nifedipine, verapamil, diltiazem, ephedrine, propanolol, metoprolol and spironolactone; thiazides such as hydrochlorothiazide and flunarizine; sydononimines such as molsidomine; sulfated polysaccharides such as heparin fractions; and the salts of such compounds with pharmaceutically acceptable acids or bases, as the case may be.

Since the inherent permeability of the skin to some drugs, such as steroids, is too low to permit therapeutic levels of such drugs to pass through a reasonably sized area of unbroken skin, it is necessary to coadminister a percutaneous absorption enhancer with such drugs. Accordingly, in such a case, a percutaneous absorption enhancer will be present in the device along with the drug, i.e., it will be present in drug reservoir layer 14 together with the drug. In addition to affecting the permeability of the skin to the drug, the enhancer may also increase the diffusivity of the drug in the reservoir layer, thus increasing the permeability of the device as a whole to the drug. Any number of the many percutaneous absorption enhancers known in the art may be used in conjunction with the present invention. For examples of suitable enhancers, see U.S. Pat. Nos. 3,996,934; 4,460,372; 4,552,872; 4,557,934 and 4,568,343 and the patents referenced therein. Preferred enhancers for use herein are those described in co-pending, commonly assigned patent application Ser. No. 07/327,312, filed 22 March 1989 and entitled "Skin Permeation Enhancer Compositions", the disclosure of which is incorporated by reference herein. A particularly preferred enhancer, as described in that patent application, is propylene glycol monolaurate (PGML). The inclusion of an enhancer in the device is optional, however, depending on the particular drug that is being administered.

As noted above, the present invention is premised on the development of a transdermal system which is biphasic and which yields substantially complete delivery of drug. That is, during an initial, delivery phase, the drug contained within drug reservoir layer 14 is delivered to the skin at a therapeutically effective rate; substantially all of the drug (i.e., greater than about 90 wt. %, more preferably greater than about 95 wt. %, most preferably greater than about 99 wt. %) initially contained within the device is delivered during this time. This initial phase is about 10 to 14 hours, typically about 12 hours. During the subsequent, secondary phase, virtually no drug (less than about 10 wt. %, preferably less than about 5 wt. %, most preferably less than about 1 wt. %) is delivered. This secondary phase is also about 10 to 14 hours, typically about 12 hours.

The present system thus enables biphasic delivery over an approximately 24-hour dosing period, wherein substantially all of the drug loaded into the device is delivered during the first half of the dosing period. The rationale behind this delivery profile is: (1) the ability to prevent or greatly reduce the onset of tolerance to the drug being administered; and (2) the elimination of the problem of residual drug. This delivery profile is effected as follows. The drug and material for the reservoir layer are selected so that: (1) the diffusivity of the drug in the reservoir layer is relatively high; and (2) the solubility of the drug in the reservoir layer is relatively low. It is preferred that the diffusion coefficient of the drug in the reservoir layer be at least about $10^{-8}$, more preferably at least about $10^{-7}$ cm$^2$/sec. It is also preferred that the solubility of the drug in the reservoir layer be less than about 10 wt. %, more preferably less than about 5 wt. %.

While the delivery profile provided herein is primarily determined by the aforementioned two factors, it is preferred that certain additional parameters be optimized as well: the thickness of the drug reservoir layer; the degree of drug loading; the partitioning rate of the drug from the reservoir to skin; and the diffusivity of the drug through skin.

Clearly, these various factors are to some extent interrelated; a thinner drug reservoir layer, for example, will be desired where the degree of drug loading is very high, i.e., where the drug is present at or above saturation. In general, however, it is preferred that the thickness of the device be in the range of about 0.001 to 0.010 inches, more preferably 0.002 to about 0.006 inches.

With respect to the remaining factors, the high diffusivity of drug in the reservoir layer, first of all, provides for a high drug concentration at the system/skin interface during the delivery phase. Since the skin is the rate-limiting layer for the delivery of many drugs, e.g., for nitroglycerin, a maximal steady-state flux is quickly established. This flux is maintained as long as there is enough drug left in the system to provide a relatively high drug concentration at the system/skin interface. When most of the drug in the system has been delivered, the concentration at the system/skin interface quickly decreases. This decrease in drug concentration at the interface is primarily effected by delivery from the interface through the skin and not by diffusion from the system to the interface.

Thus, a high drug diffusion coefficient—at least about $10^{-8}$ cm$^2$/sec, more preferably at least about $10^{-7}$ cm²/sec, as noted above—provides for both a high steady-state flux and a rapid decrease in flux actuated by drug depletion.

The relatively low solubility of drug in the reservoir layer allows for the attainment of a high drug thermodynamic activity (necessary for maximal flux) with a relatively small total amount of drug. Conventional transdermal nitroglycerin systems, by contrast, contain a large excess of drug in order to maintain the necessary thermodynamic driving force.

With respect to drug loading and delivery, the duration of the delivery phase is determined both by: (1) the total amount of drug in the system, which is in turn determined by the reservoir thickness and drug concentration in the reservoir; and (2) the delivery rate, which is a function of the drug to be delivered and its skin permeability. A given drug loading value will provide a certain duration of delivery, depending on the delivery rate; that is, drug loading (in, e.g., milligrams) is equivalent to the delivery rate (e.g., milligrams/hr) times duration of delivery (hr). And, since the delivery rate is dependent on the inherent permeability of the drug, controlled modulation of duration is typically accomplished by varying drug loading. Due to the uncontrollable inter- and intra-subject variability in drug permeability, a certain amount of variability in duration also results with a given loading value.

To administer a drug using the present device, the basal surface of the device defined by the drug reservoir layer is adhered to the skin. The drug is preferably delivered to a skin area of about 5 to 50 cm², more preferably 5 to 20 cm². As the length of the "on" phase (i.e., the initial, delivery phase) is about 10 to 14 hours, and the length of the "off" phase (i.e., the subsequent, secondary phase) is also about 10 to 14 hours, the total dosing period is about 20 to 28 hours, most preferably, as noted previously, about 24 hours. The patch may thus be removed and replaced every day at about the same time.

An exemplary embodiment of the present invention is a biphasic system for delivering nitroglycerin transdermally. In a nitroglycerin system, the preferred material for the drug reservoir layer is a silicone adhesive, selected so that the diffusion coefficient and solubility of the nitroglycerin in the reservoir meet the above-defined criteria. To achieve the known desirable blood levels of the drug, the delivery rate during the initial phase is preferably in the range of about 10 to 50 $\mu g/cm^2/hr$, more preferably in the range of about 20 to 40 $\mu g/cm^2/hr$.

Fabrication: The device of the present invention is readily manufactured as follows. Drug is incorporated into the reservoir adhesive material by, first, preparing a solution of drug, adhesive and solvent. This admixture is then cast onto a release liner layer, and solvent is removed by heating. To this drug reservoir/release liner composite is laminated a sheet of backing. Individual devices of the desired size may then be cut from this laminated composite.

It is to be understood that while the invention has been described in conjunction with the preferred specific embodiment thereof, that the foregoing description as well as the examples which follow are intended to illustrate and not limit the scope of the invention. Other aspects, advantages and modifications within the scope of the invention will be apparent to those skilled in the art to which the invention pertains.

A solution of 0.40 wt. % nitroglycerin (from a 10 wt. % solution in ethanol), 1.98 wt. % Dow Corning Medical Silicone Fluid 360 100 acts and 17.40 wt. % Dow Corning Medical Silicon Adhesive 355 in freon (1,1,2-trichloro-2,2,1-trifluoroethane) was prepared. This nitroglycerin/silicone adhesive solution was cast onto a fluorocarbon-coated polyester release liner (3M, Scotchpak 1022) at a thickness of 0.015". The solvent was removed by heating at 50° C. for 10 minutes, producing a 0.003" thick drug reservoir layer containing 2.0 wt. % nitroglycerin and 10.0% silicone fluid. To this drug reservoir layer was laminated a 0.0013" sheet of medium density polyethylene/polyester laminate film to serve as the backing layer, with the polyester side in contact with the drug reservoir layer.

In vitro permeation studies with human cadaver epidermis indicated that the system delivered nitroglycerin at 20 to 40 $\mu g/cm^2/hr$ during an initial phase of 6–8 hours, followed by a rapid decrease in delivery to essentially zero.

Figure 2:
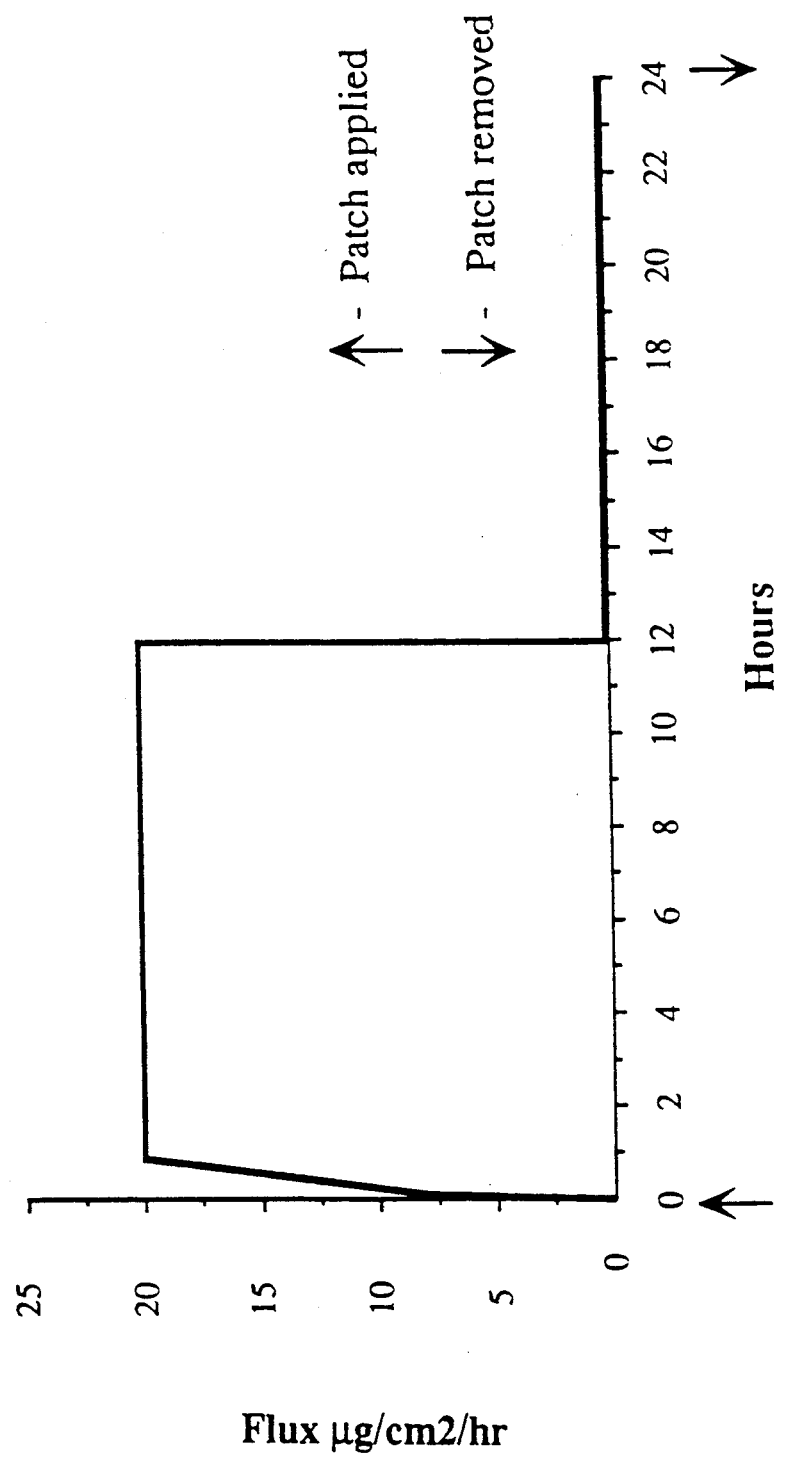
FIG. 2 is a graph which illustrates the ideal flux profile for a biphasic nitroglycerin system.
Figure 3:
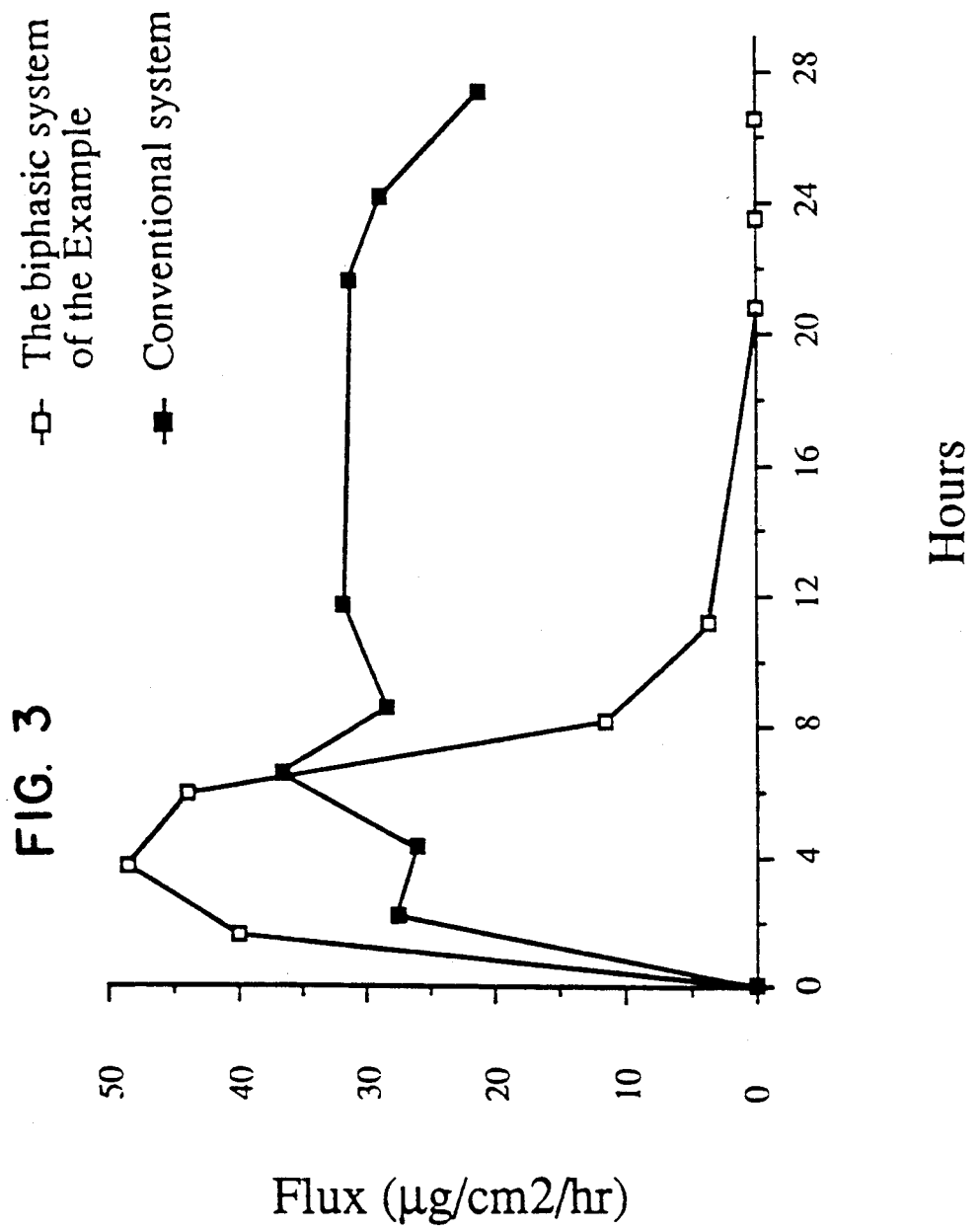
FIGS. 3 and 4 are graphs illustrating the flux profiles (FIG. 3) and cumulative drug delivered (FIG. 4) for a conventional transdermal nitroglycerin system and for the system of the invention.
Figure 4:
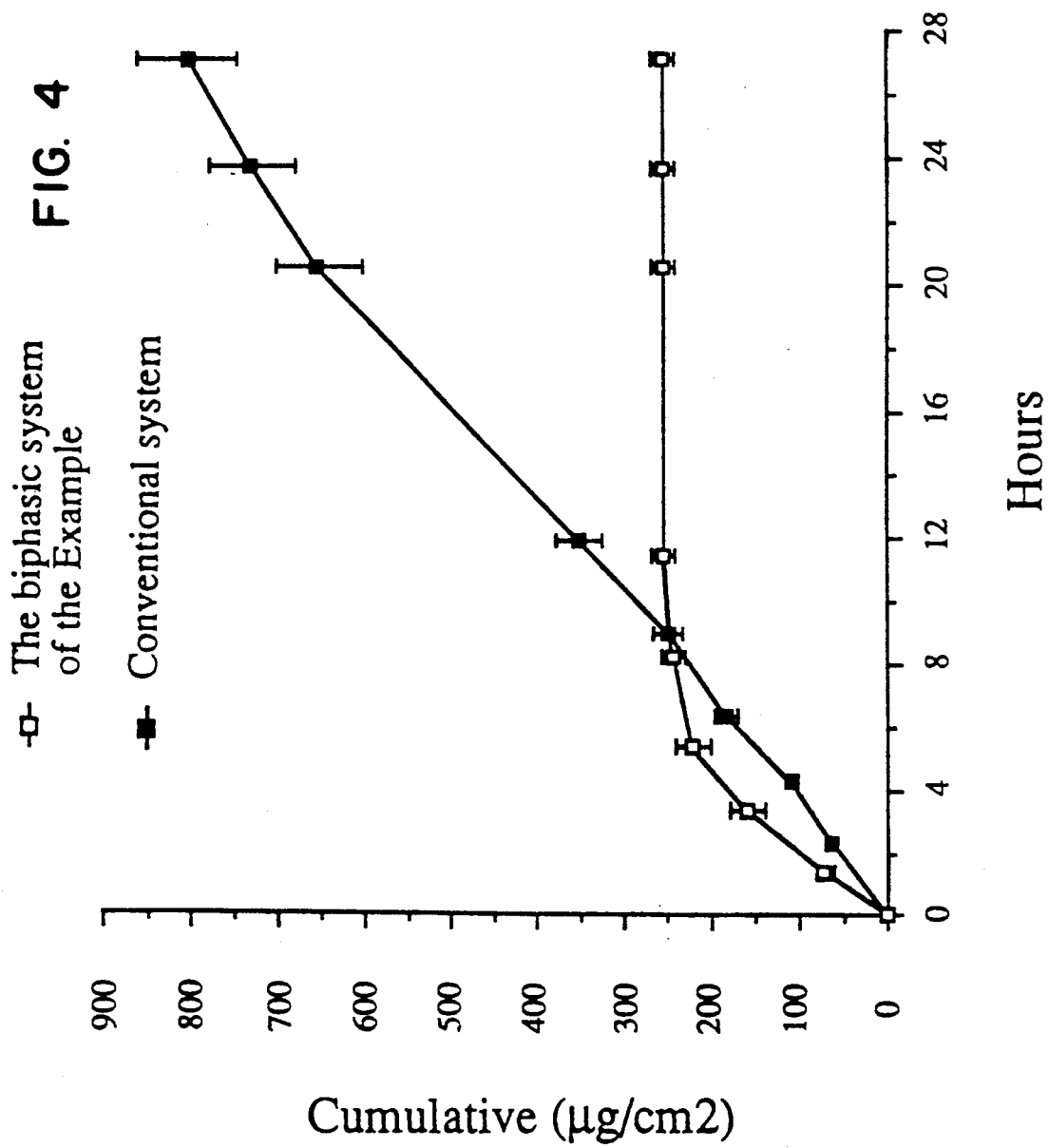

FIG. 2 is a graph illustrating the ideal flux profile for a biphasic nitroglycerin system, i.e., a delivery rate equal to that of constant delivery systems for 12 hours, followed by a rapid decrease to zero delivery for the remaining period of the dosing interval. FIGS. 3 and 4 graphically illustrate the flux profiles (FIG. 3) and cumulative drug delivered (FIG. 4) obtained for a conventional transdermal nitroglycerin system (Alza's Transderm-Nitro ®) and for the system of the invention as described hereinabove.

We claim:

1. A biphasic transdermal drug delivery device for delivering a drug contained therein at therapeutically effective rates during an initial, delivery phase, but which during a subsequent, secondary phase, delivers substantially no drug, the device comprising:
   (a) a backing layer that is substantially impermeable to the drug and defines the face surface of the device; and
   (b) an adhesive drug reservoir layer that defines the basal surface of the device during use and contains an initial quantity of the drug,
   wherein the diffusion coefficient of the drug in the reservoir layer is at least about $10^{-8}$ cm²/sec, and the solubility of the drug in the reservoir layer is less than about 10 wt. %, and further wherein the delivery phase includes a period of time from the application of the device to a patient to a time about 10 to 14 hours thereafter during which time more than 90 wt. % of the initial quantity of the drug is delivered.

2. The device of claim 1, wherein the delivery phase includes a period of time from the application of the device to a patient to a time about 12 hours thereafter, and further wherein less than 10 wt. % of the drug is delivered during the secondary phase.

3. The device of claim 1, wherein more than 95 wt. % of the initial quantity of drug is delivered during the delivery phase and wherein less than 5 wt. % of the drug is delivered during the secondary phase.

4. The device of claim 3, wherein more than 99 wt. % of the initial quantity of drug is delivered during the delivery phase and wherein less than 1 wt. % of the drug is delivered during the secondary phase.

5. The device of claim 1, wherein the diffusion coefficient of the drug in the reservoir layer is at least about $10^{-7}$ cm²/sec 6. The device of claim 1, wherein the solubility of the drug in the reservoir layer is less than about 5 wt. %.

7. The device of claim 1, wherein the thickness of the device is in the range of about 0.001 to 0.010 inches.

8. The device of claim 1, wherein the thickness of the device is in the range of about 0.002 to 0.006 inches.

9. The device of claim 2, wherein the subsequent, secondary phase is about 10 to 14 hours.

10. The device of claim 9, wherein the subsequent, secondary phase is about 10 to 14 hours.

11. The device of claim 1, further including a release liner layer that covers the basal surface defined by the drug reservoir layer and adapted to be removed from the device prior to use to expose said basal surface.

12. The device of claim 1, wherein the drug reservoir layer is comprised of a silicone adhesive 13. The device of claim 1, wherein the drug reservoir layer additionally includes a skin permeation enhancer.

14. The device of claim 13, wherein the skin permeation enhancer comprises propylene glycol monolaurate or propylene glycol monolaurate in combination with propylene glycol dilaurate.

15. The device of claim 14, wherein the skin permeation enhancer comprises propylene glycol monolaurate.

16. The device of claim 1, wherein the drug is nitroglycerin.

17. The device of claim 16, wherein the therapeutically effective rate is in the range of about 10 to 50 $\mu g/cm^2/hr$.

18. The device of claim 17, wherein the therapeutically effective rate is in the range of about 20 to 40 $\mu g/cm^2/hr$.

19. A biphasic transdermal drug delivery device for delivering greater than 90 wt. % of a drug initially contained therein at therapeutically effective rates during an initial, delivery phase of about 10 to 14 hours, but which during a subsequent, secondary phase, delivers substantially no drug, the device comprising:
 (a) a backing layer that is substantially impermeable to the drug and defines the face surface of the device; and
 (b) a drug reservoir layer comprised of a silicone adhesive that defines the basal surface of the device during use and contains the drug,
 wherein the diffusion coefficient of the drug in the reservoir layer is at least about $10^{-7}$ cm$^2$/sec, the solubility of the drug in the reservoir layer is less than about 10 wt. %, the thickness of the device is in the range of about 0.002 to 0.006 inches, and the drug is nitroglycerin.

* * * * *